United States Patent

Kuragano et al.

Patent Number: 5,196,578
Date of Patent: Mar. 23, 1993

[54] PURIFICATION PROCESS OF METHACRYLIC ACID

[75] Inventors: Morimasa Kuragano, Sakai; Takeshi Isobe; Nobutaka Ueda, both of Takaishi; Minoru Koshibe, Sakai; Yoshihiro Sezaki, Izumi; Hirozo Segawa, Niigata; Katsuji Yoguchi, Niigata; Rensuke Ikarashi, Niigata, all of Japan

[73] Assignees: Mitsui Toatsu Chemicals, Incorporated, Tokyo; Kuraray Co., Ltd., Kurashiki, both of Japan

[21] Appl. No.: 758,362

[22] Filed: Sep. 10, 1991

Related U.S. Application Data

[63] Continuation of Ser. No. 211,262, Jun. 24, 1988, abandoned.

[30] Foreign Application Priority Data

Oct. 9, 1987 [JP] Japan .................. 62-253808
Oct. 12, 1987 [JP] Japan .................. 62-254687
Feb. 4, 1988 [JP] Japan .................. 63-22921

[51] Int. Cl.$^5$ .................. C07C 51/16; C07C 51/235; C07C 51/42
[52] U.S. Cl. .................. 562/531; 562/532; 562/545; 562/600
[58] Field of Search .............. 562/600, 532, 531, 545; 203/DIG. 21, 59

[56] References Cited

U.S. PATENT DOCUMENTS 3,893,895 7/1975 Dehnert et al. .............. 562/600 X
4,001,317 1/1977 Grasselli et al. .
4,301,031 11/1981 Shaw et al. .

Primary Examiner—José G. Dees
Assistant Examiner—Joseph M. Conrad
Attorney, Agent, or Firm—Oblon, Spivak, McClelland, Maier & Neustadt

[57] ABSTRACT

A process is provided for the purification of methacrylic acid. The process can easily remove dibasic acids and aldehydes containing in trace amounts as impurities. According to the process, crude methacrylic acid obtained as an aqueous solution by vapor-phase catalytic oxidation of isobutylene, tertiary butanol, methacrolein or isobutyl aldehyde is treated with at least one compound selected from the group consisting of m-aminophenol, m-phenylenediamine, 2,4-diaminotoluene and 2,4-diamino-diphenylamine, followed by distillation, optionally, in the presence of a p-phenylene diamine.

4 Claims, 1 Drawing Sheet

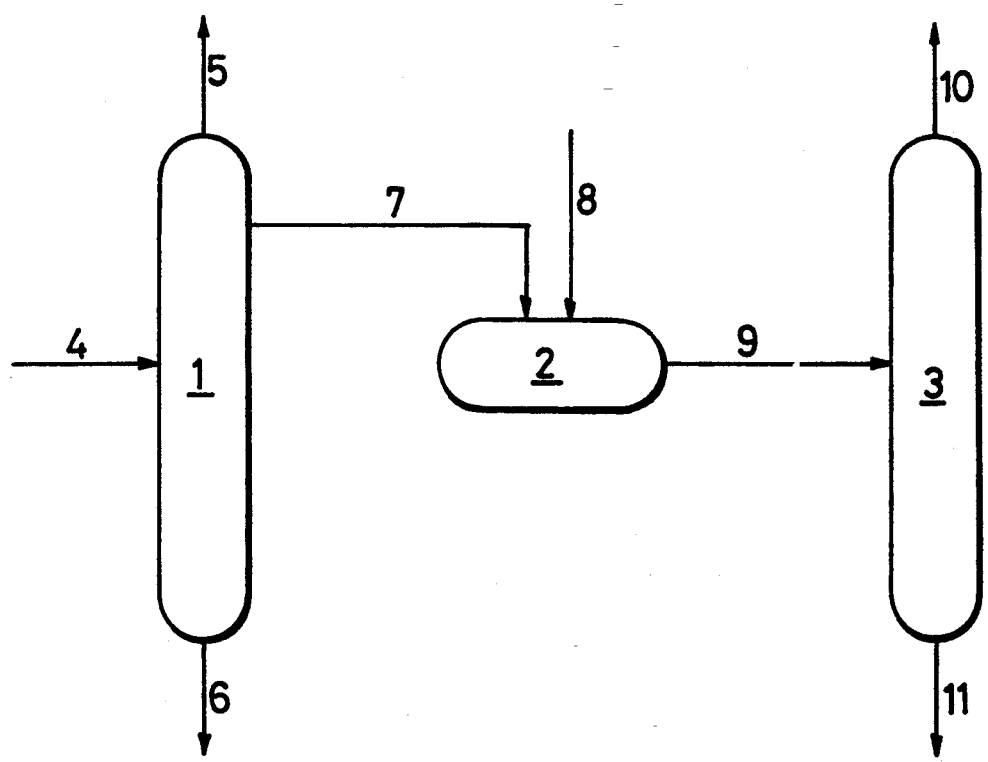

PURIFICATION PROCESS OF METHACRYLIC ACID

This application is a continuation of application Ser. No. 07/211,262, filed on Jun. 24, 1988, now abandoned.

BACKGROUND OF THE INVENTION

1) Field of the Invention

This invention relates to a process for removing impurities from crude methacrylic acid obtained as an aqueous solution by vapor-phase catalytic oxidation of isobutylene or the like.

2) Description of the Prior Art

Regarding the production of methacrylic acid by catalytic oxidation of isobutylene, tertiary butanol, methacrolein or isobutyl aldehyde with molecular oxygen in the presence of steam in accordance with a single-stage or two-stage reaction, a number of proposals have been made including, for example, catalytic reactions disclosed in U.S. Pat. Nos. 4,001,317, 4,301,031 and so on, purification and recovery methods and processes disclosed in various publications, etc. A reaction gas obtained in such a manner contains byproducts in addition to methacrylic acid as the target product, for example, carboxylic acids such as formic acid, acetic acid, propionic acid, maleic acid, citraconic acid, benzoic acid, toluic acid and terephthalic acid, and aldehydes such as formaldehyde, acetaldehyde, propionaldehyde, methacrolein, benzaldehyde, tolualdehyde and furfural. Most of these impurities can be removed by a conventional purification method such as extraction or distillation. It is however difficult to remove impurities which are contained in trace amounts. For example, it is difficult to remove maleic acid, citraconic acid and aldehydes completely. When aldehydes are contained in particular, absorption is observed in the ultraviolet range, and inconvenient problems arise in many instances such that at the time of a polymerization reaction, the polymerization is suppressed to require longer reaction time and the resulting polymer is tinged.

As a method for removing aldehydes from methacrylic acid in which the aldehydes are contained, it has been known to add an amine such as hydrazine, ethylenediamine, aniline or polyamine (Japanese Patent Laid-Open No. 23017/1977), ethylene glycol (Japanese Patent Laid-Open No. 128336/1983), a bisulfite (Japanese Patent Laid-Open No. 252446/1985), a mercaptan (Japanese Patent Laid-Open No. 6635/1985), resorcin, pyrogallol or a-naphthol (Japanese Patent Laid-Open No. 130546/1985), or the like.

However, the use of the above-described amine cannot bring about sufficient effects for the removal of aldehydes and moreover, tends to induce polymerization in a distillation step to be performed after the treatment. Glycols, bisulfites and mercaptans cannot exhibit strong effects for the removal and must hence be added in a large amount, whereby such additives cause secondary contamination or reaction loss of methacrylic acid. On the other hand, phenols such as resorcin can exhibit removal effects only in the co-presence of a strongly acidic substance such as sulfuric acid or hydrochloric acid. Accordingly, they render the operation complex and requires the selection of high-quality materials for actual facilities.

SUMMARY OF THE INVENTION

A first object of this invention is therefore to provide a process for the purification of methacrylic acid, which permits easy removal of dibasic acids and aldehydes, which are contained in trace amounts in crude methacrylic acid obtained by vapor-phase catalytic oxidation of a compound having 4 carbon atoms such as isobutylene, without secondary contamination due to substances added and without need for the selection of high-quality materials for facilities.

A second object of this invention is to provide a a purification stage which is more effective than the above-mentioned purification step of the crude methacrylic acid.

A third object of this invention is to provide a purification process which features less coloration of distilled methacrylic acid and less formation of insoluble matter in a bottom.

The first object of this invention can be attained by treating crude methacrylic acid, which has been obtained by vapor-phase catalytic oxidation of isobutylene, tertiary butanol, methacrolein or isobutyl aldehyde, with at least one compound selected from the group consisting of m-aminophenol, m-phenylenediamine, 2,4-diaminotoluene and 2,4-diaminodiphenylamine and then subjecting the thus-treated methacrylic acid to distillation.

The second object of this invention can be achieved by subjecting the crude methacrylic acid obtained by the oxidation to distillation in advance in a distillation column, treating with said at least one compound a fraction drawn out from an intermediate stage of an enriching section of the distillation column, and then subjecting the thus-treated fraction to distillation.

The third object of this invention can be fulfilled by subjecting the crude methacrylic acid or fraction, which has been treated with said at least one compound, to distillation in the presence of at least one p-phenylenediamine represented by the following general formula (I):

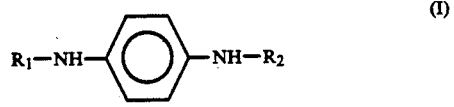

(I)

wherein $R_1$ means a hydrogen atom or a $C_3$–$C_6$-alkyl, phenyl, p-tolyl, p-methoxyphenyl or $\beta$-naphthyl group and $R_2$ denotes a hydrogen atom or a phenyl, p-tolyl or $\beta$-naphthyl group.

BRIEF DESCRIPTION OF THE DRAWING

FIG. 1 illustrates one example of apparatus suitable for uses in the practice of the purification process of this invention, in which there are shown a first distillation column 1, a treating tank 2, a second distillation column 3, a crude methacrylic acid feed line 4, an overhead discharge line 5, a discharge line 6 for high boiling products, a draw out line 7 from an enriching section of the distillation column, a compound feed line 8, a treating product guide line 9, a distillation line 10 for purified methacrylic acid, and a discharge line 11 for high boiling bottoms. The process of this invention will hereinafter be described in detail on the basis of the illustrated apparatus.

DETAILED DESCRIPTION OF THE INVENTION

Methacrylic acid is usually obtained by catalytically oxidizing isobutylene, tertiary butanol, methacrolein or isobutyl aldehyde in a single catalyst layer or two catalyst layers. In such a process, methacrylic acid is extracted out with a solvent from an aqueous solution, which has been collected by cooling and condensing a reaction product gas which contains methacrylic acid, and is then purified by a distillation procedure which comprises a step for the separation of the extracting solvent, another step for the separation of light distillates, and a further step for the separation of heavy distillates.

The crude methacrylic acid to be processed in accordance with the process of this invention may be crude methacrylic acid obtained from any one of the above-described steps. Namely, the present invention may be applied to any crude methacrylic acid such as the aqueous solution of methacrylic acid, the extract containing methacrylic acid, the methacrylic acid obtained after the removal of the extracting solvent and light distillates, and the methacrylic acid obtained subsequent to the removal of the heavy distillates. In order to obtain maximum removal effects by an additive in a smallest proportion, it is however desirable to apply this invention to the methacrylic acid obtained after the removal of the light distillates. Namely, it is desirable to apply this invention to methacrylic acid obtained subsequent to the removal of low boiling products such as acetic acid, acrylic acid, propionic acid and isobutyric acid or to methacrylic acid which has been obtained after the subsequent separation of a portion of maleic acid, polymerization inhibitor, polymer and other high boiling products as bottoms and is to be subjected to final superfractionation. As a further preferable embodiment, it is preferable to use a methacrylic acid fraction containing less aldehydes in order to obtain maximum removal effects. For this purpose, it is desirable to apply this invention to a methacrylic acid fraction drawn out from an intermediate stage of an enriching section of a distillation column which, for example, serves to remove the heavy distillates from the methacrylic acid obtained after removal the extracting solvent and light distillates. The fraction drawn out from the intermediate stage of the enriching section of the distillation column is generally reduced by 50% or so in terms of aldehyde contents compared with a fraction obtained from the top of the distillation column and is most suitable as crude methacrylic acid to be processed by the process of this invention. Methacrylic acid obtained from the top of distillations column may be used, as is, as a raw material for the production of methyl methacrylate. Regarding the term "intermediate stage of the enriching section of the distillation column" as used herein, a section above a feeding port of the distillation column is called "enriching section" and the intermediate stage is located between a top of the distillation column and the feeding port, for example, feeding line 4 at a height $\frac{1}{4}$-$\frac{3}{4}$ the way down from the top of the distillation column toward the feeding port, for example, feeding line 4 of the distillation column, preferably, about $\frac{1}{2}$ the way down from the top.

In the present invention, m-aminophenol, m-phenylenediamine, 2,4-diaminotoluene or 2,4-diaminodiphenylamine may be used in at least an equimolar amount, preferably in at least a twofold molar amount, most preferably in at least a threefold molar amount, all, based on carboxylic acid groups derived from unsaturated dibasic acids and aldehyde groups contained in methacrylic acid. It is difficult to precisely analyze various impurities contained in trace amounts in an actual solution in a production step of methacrylic acid. Although the amount of the additive varies depending what separation and purification steps methacrylic acid to be processed in accordance with this invention has been subjected to, the additive may generally be used in a molar amount 3-10 times based on carboxylic acid groups, derived from unsaturated dibasic acids, and aldehyde groups which can both be analyzed quantitatively.

The treatment of methacrylic acid with m-aminophenol, m-phenylenediamine, 2,4-diaminotoluene or 2,4-diaminodiphenylamine may be achieved by simply mixing them together at room temperature. It is however preferable to heat them to a temperature in a range of 50°-100° C. in order to complete the reactive treatment in a short period of time. Although the time of the treatment may usually be from 1 minute to 60 minutes, such a separate heating step may be omitted because the methacrylic acid added with the above compound is usually heated in the next distillation step. The treatment may therefore be effected by a simple procedure, for example, by adding the above compound in a predetermined amount to a feed liquid to be fed to a distillation column for methacrylic acid, to a still liquid or to the interior of the column.

Upon distillation of methacrylic acid, it is widely practiced to use a polymerization inhibitor in order to prevent polymerization. In particular, hydroquinone, hydroquinone monomethyl ether, phenothiazine and the like are known well. In the process of this invention for the removal of impurities, polymerization may still take place in some instances during distillation when these conventional polymerization inhibitors are used. Depending on a raw liquid to be processed, a polymerization inhibitor to be used, the structure of a distillation column, operational conditions for the distillation column and the manner of operation, polymerized substances may occur inside the distillation column and/or the still liquid so that long-term continuous distillation may be rendered infeasible. The present inventors have carried out a further investigation in this regard. As a result, it has been found that the combined use of at least one p-phenylenediamine represented by the general formula (I) can exhibit outstanding effects for the prevention of polymerization upon treatment of methacrylic acid, which has been obtained by vapor-phase catalytic oxidation, with the compound specified in this invention.

As specific examples of the p-phenylenediamine of the general formula (I) useful as a polymerization inhibitor in this invention, may be mentioned N,N'-diphenyl-p-phenylenediamine, N,N'-ditolyl-p-phenylenediamine, N,N'-di-β-naphthyl-p-phenylenediamine, N-phenyl-N'-tolyl-p-phenylenediamine, N-phenyl-N'-isopropyl-p-phenylenediamine, N-phenyl-N'-(1,3-dimethylbutyl)-p-phenylenediamine, N-(p-methoxyphenyl)-p-phenylenediamine, 4-aminodiphenylamine and p-phenylenediamine. The amounts of these polymerization inhibitors to be used vary depending on conditions under which they are used. They may generally be used in an amount of 0.005-1.0 wt. %, preferably 0.01-0.5 wt. %, both, based on methacrylic acid or its solution to be fed to a distillation column. In addition, no problem or inconvenience will arise from its combined use with a conventional polymerization inhibitor such as hydroquinone, hydroquinone monomethyl ether or phenothiazine.

achieved with respect to maleic acid and furfural and at least 97% removal has also been attained regarding benzaldehyde.

TABLE 1

| Impurity | Crude methacrylic acid | Impurity Contents (unit: ppm) Additive | | | | |
|---|---|---|---|---|---|---|
| | | None | m-Aminophenol | m-Phenylenediamine | 2,4-Diaminotoluene | 2,4-Diaminodiphenylamine |
| Acetic acid | 30 | 55 | 50 | 40 | 50 | 40 |
| Acrylic acid | 70 | 80 | 75 | 75 | 80 | 60 |
| Isobutyric acid | 450 | 510 | 510 | 500 | 520 | 450 |
| Maleic acid | 25 | 20 | ≦1 | ≦1 | ≦1 | ≦1 |
| Furfural | 40 | 45 | ≦1 | ≦1 | ≦1 | ≦1 |
| Benzaldehyde | 130 | 90 | 5 | ≦1 | ≦1 | 5 |
| Other carbonyl compounds | 80 | 50 | 5 | 5 | 5 | 5 |
| Polymerization inhibitor | 2170 | 60 | 65 | 60 | 60 | 65 |
| High boiling components | 670 | 410 | 260 | 210 | 280 | 250 |
| Non-volatile components | 2300 | 0 | 0 | 0 | 0 | 0 |
| Water | 600 | 900 | 800 | 900 | 900 | 600 |
| Absorbance (−log T) | | 0.860 | 0.027 | 0.025 | 0.028 | 0.036 |

The stage of treatment between crude methacrylic acid and the specified compound, which stage is adopted in a preferred embodiment of this invention, will hereinafter be described in further detail with reference to FIG. 1.

Crude methacrylic acid, from which light distillates, extracting solvent and the like have been removed, is fed via the feeding line 4 to the first distillation column 1 which serves to remove high boiling components. In the first distillation column 1, a portion is distilled out from the top of the column, another portion is drawn out from an intermediate stage of an enriching section, and the remaining portion is discharged as high boiling components from the bottom of the column. The fraction from the top is delivered to a next esterification step via the line 5, while the fraction drawn out from the intermediate stage of the enriching section of the column 1 is fed to the treating tank 2 via the line 7 and after subjecting it to treatment with the compound specified in this invention and charged, e.g., in a form dissolved in high-purity methacrylic acid by way of the line 8, the resulting mixture is fed to the second distillation column 3. In the second distillation column 3, purified methacrylic acid from which aldehydes and the like have been removed is distilled out from the top, while the specific compound reacted with the aldehydes and the like, such as m-aminophenol, and unreacted substances are discharged as bottoms along with high boiling components from the bottom.

EXAMPLE 1

Isobutylene was subjected to vapor-phase catalytic oxidation. Distillates were cooled, condensed and collected. An aqueous solution of methacrylic acid, thus obtained, was processed by a thickener and a byproduced solid was separated. Thereafter, methacrylic acid was extracted with hexane. Hexane and low boiling components were distilled off from the extract, thereby obtaining crude methacrylic acid described in Table 1. m-Aminophenol, m-phenylenediamine, 2,4-diaminotoluene and 2,4-diaminodiphenylamine were added separately in a molar amount 7 times the sum of carboxyl groups derived from maleic acid in the crude methacrylic acid and aldehyde groups derived from furfural and benzaldehyde in the crude mathacrylic acid. Batch distillation was conducted under the same conditions. The contents of impurities in each methacrylic acid distilled are also shown in Table 1. It has been confirmed that substantially 100% removal has been Coloration of distilled methacrylic acid The absorbance of each distilled methacrylic acid (as measured in terms of −log T at 350 nm, using a 10 mm thick glass cell) is also shown in Table 1. The table indicates that the coloration has been improved significantly by the treatment with each of the compounds specified in this invention.

EXAMPLE 2

Tertiary butanol was subjected to vapor-phase catalytic oxidation, and an extract of methacrylic acid was obtained in the same manner as in Example 1. Crude methacrylic acid, which has been obtained by distilling off the extracting solvent from the extract, contained 50 ppm of maleic acid, 110 ppm of furfural and 140 ppm of benzaldehyde. Ten kilograms of the crude methacrylic acid were added with 10 g of 2,3-diaminotoluene, and the resultant mixture was distilled under reduced pressure to remove low boiling components, thereby to obtain 8.7 kg of bottoms. Since the bottoms formed a little solid matter, the solid matter was filtered off. The filtrate was then continuously distilled at a reflux ratio of 0.5 in a 20-stage Oldershaw column, whereby 7.6 kg of methacrylic acid was obtained as a final product. The contents of impurities contained in the final product were lower than the detection limits of gas chromatograph and liquid chromatograph. In contrast, methacrylic acid obtained by following the above procedure without any additive still contained 25 ppm of maleic acid, 90 ppm of furfural and 100 ppm of benzaldehyde.

EXAMPLE 3

An aqueous solution of methacrylic acid was obtained by subjecting tertiary butanol and a molecular oxygen containing gas to a vapor-phase catalytic reaction in the presence of an oxidizing catalyst and then quenching the resultant high-temperature reaction product gas. After removing light distillates such as methacrolein from the aqueous solution, methacrylic acid was extracted with hexane. Hexane and low boiling components were distilled off from the extract, so that crude methacrylic acid shown in Table 2 was obtained. The crude methacrylic acid was purified in accordance with the flow depicted in FIG. 1. Incidentally, the outlines of the distillation columns and treating tank are summarized in Table 3.

The crude methacrylic acid was fed at 20 kg/hr to the first distillation column 1 which was operated at a top temperature of 95° C., a pressure of 60 mmHg and a reflux ratio of 0.5. Methacrylic acid which distilled out at 12 kg/hr from the top was delivered to a subsequent esterification step (not shown in the drawing) as a raw material for the production of methyl methacrylate. A fraction was drawn out at a rate of 6 kg/hr from the intermediate stage of the enriching section and was then supplied to the treating tank 2. A solution, which contained 1 wt. % of m-phenylenediamine and 1 wt. % of N-phenyl-N'-isopropyl-p-phenylenediamine in high-purity methacrylic acid and was charged at 0.3 kg/hr to the treating tank 2 which had been controlled to 60° C. Thereafter, the treating mixture was guided at 6.3 kg/hr to the second distillation column 3 so that the treatment of the fraction from the intermediate stage of the enriching section was performed for about 30 minutes. Likewise the first distillation column 1, the second distillation column 3 was operated at a top temperature 95° C., a pressure of 60 mmHg and a reflux ratio of 0.5 so that purified methacrylic acid was obtained at 4.3 kg/hr from the top. On the other hand, m-phenylenediamine which reacted with aldehydes and the like, and high boiling components, were obtained at 2.0 kg/hr from the bottom. Table 2 shows the compositions of the crude methacrylic acid, the overhead of the first distillation column, the fraction drawn out from the intermediate stage of the enriching section and the overhead of the second distillation column as well as the absorbances of the overheads and fraction.

The methacrylic acid drawn out from the intermediate stage of the enriching section of the first distillation column contained aldehydes at the low concentrations, and was hence treated successfully with the small amount of m-phenylenediamine so that its coloration was improved significantly.

EXAMPLE 4

The procedure of Example 3 was repeated except that 1 wt. % of m-phenylenediamine dissolved in high-purity methacrylic acid was changed to 1 wt. % of m-aminophenol. Absorbance was measured with respect to the overhead of the second distillation column. As a result, purified methacrylic acid having 0.03 as −log T and improved in coloration was obtained.

TABLE 2

| | Crude methacrylic acid | First distillation column Overhead | First distillation column Intermediate stage fraction of enriching section | Overhead of second distillation column (unit: ppm) |
| --- | --- | --- | --- | --- |
| Impurity | | | | |
| Acetic acid | 30 | 50 | 30 | 40 |
| Isobutyric acid | 450 | 500 | 300 | 320 |
| Acrylic acid | 70 | 100 | 80 | 90 |
| Maleic acid | 25 | 25 | 25 | ≦1 |
| Furfural | 40 | 50 | 25 | ≦1 |
| Benzaldehyde | 130 | 120 | 50 | 5 |
| Other carbonyl compounds | 80 | 70 | 10 | ≦1 |
| Polymerization inhibitor | 2170 | 50 | 50 | 60 |
| High boiling components | 670 | 100 | 120 | 80 |
| Non-volatile components | 2300 | 0 | 0 | 0 |
| Water | 500 | 700 | 400 | 550 |
| Absorbance (−log T) | | 0.30 | 0.15 | 0.03 |

TABLE 3

| | First distillation column | Treating tank | Second distillation column |
| --- | --- | --- | --- |
| Type | Packed column | Stirred tank | Packed column |
| Specification | 6B × 16 m | 5 l | 6B × 14 m |
| Material | SUS 316 | SUS 316 | SUS 316 |
| Enriching section | 6 m tall, packed with Paul rings; draw-out port in middle stage of 3 m high | — | 4 m tall, packed with Paul rings |
| Recovery section | 6 m tall, packed with Paul rings | — | 4 m tall, packed with Paul rings |

COMPARATIVE EXAMPLE 1

The procedure of Example 3 was repeated except for the replacement of m-phenylenediamine by aniline. Absorbance was measured with respect to the overhead of the second distillation column. As a result, −log T was found to be 0.15 so that no improvement was observed in the coloration.

EXAMPLE 5

In a process as in Example 3, m-phenylenediamine was charged directly to the second distillation column without the treatment in the treating tank. Results similar to those obtained in Example 3 were obtained.

EXAMPLES 6–10

Portions of the intermediate-stage fraction of the enriching section of the first distillation column, which had been obtained in Example 3, were added with their corresponding additives shown in Table 4 in a amount 5 times in mole the sum of maleic acid, furfural and benzaldehyde. The resultant mixtures were separately distilled at an operation pressure of 60 mmHg and a reflux ratio of 0.5 by means of a 20-stage Oldershaw column. The absorbances of methacrylic acid samples thus obtained were measured. Results are also shown in Table 4.

TABLE 4

| Example | Compound added | Maleic acid | Furfural | Benzaldehyde | Other carbonyl compounds | (unit: ppm) Asorbance (−log T) |
| --- | --- | --- | --- | --- | --- | --- |
| 6 | m-Phenylenediamine | ≦1 | ≦1 | 5 | ≦1 | 0.03 |
| 7 | m-Aminophenol | ≦1 | ≦1 | 5 | 5 | 0.04 |
| 8 | 2,4-Diaminodiphenylamine | ≦1 | ≦1 | 5 | ≦1 | 0.03 |
| 9 | 2,4-Diaminotoluene | ≦1 | ≦1 | 5 | ≦1 | 0.03 |

TABLE 4-continued

| Example | Compound added | Maleic acid | Furfural | Benzaldehyde | Other carbonyl compounds | (unit: ppm) Asorbance (−log T) |
|---|---|---|---|---|---|---|
| 10 | m-Phenylenediamine + 2,4-diaminodiphenylamine | ≦1 | ≦1 | 5 | ≦1 | 0.03 |
| Intermediate-stage fraction of enriching section | | 25 | 25 | 50 | 10 | 0.15 |

EXAMPLE 11

Crude methacrylic acid, which had been obtained by vapor-phase catalytic oxidation of isobutylene, was purified to obtain methacrylic acid containing 300 ppm of hydroquinone monomethyl ether. Portions of the methacrylic acid were added with 100 ppm of their corresponding compounds specified in the present invention and 200 ppm of their corresponding polymerization inhibitors of various kinds. Fifty grams of each of the resultant mixtures were placed in a 100-ml eggplant-type flask fitted with a packed column of 20 cm tall. Distillation was then conducted by a conventional method while continuously feeding the same methacrylic acid at 80 g/hr. After continuously conducting the distillation at a pressure of 50 mmHg and a flask liquid temperature of 92°–95° C. for 1.5 hours, insoluble matter in the distillation residue (about 125–130 g) was filtered off.

Effects of the additives

The coloration (−log T) of each distilled methacrylic acid at 340 nm was measured by using a 10 mm thick glass cell. Results are shown in Table 5, in which circle ◯ indicates 0.01 or smaller while letter X shows 0.05 or greater.

Effects of the polymerization inhibitors

The concentration of insoluble matter in each distillation residue was measured. Results are also shown in Table 5, in which circle ◯ indicates 100 ppm or lower, triangle Δ shows 100–200 ppm and letter X designates 1000 ppm or higher. In the table Experiment Nos. 1–9 are each directed to an illustrative example of the combined use of one of the compounds specified in the present invention and a polymerization inhibitor, whereas Experiment Nos. 10–15 are individually directed to an illustrative example in which a conventional polymerization inhibitor was used in combination with one of the compounds specified in this invention or neither any one of the compounds specified in the present invention nor any polymerization inhibitor were employed. Incidentally, Experiment Nos. 11 and 13 are directed respectively to examples in which the polymerization inhibitors were both increased to 500 ppm.

TABLE 5

| Experiment No. | Added compound | Polymerization inhibitor | Coloration | Insoluble matter |
|---|---|---|---|---|
| 1 | m-Aminophenol | A | ◯ | ◯ |
| 2 | " | B | ◯ | ◯ |
| 3 | " | C | ◯ | Δ |
| 4 | m-Phenylenediamine | A | ◯ | ◯ |
| 5 | " | D | ◯ | ◯ |
| 6 | " | E | ◯ | ◯ |
| 7 | 2,4-Diaminotoluene | D | ◯ | ◯ |
| 8 | " | F | ◯ | ◯ |
| 9 | " | G | ◯ | ◯ |
| 10 | m-Aminophenol | MEQ | ◯ | X |
| 11 | " | MEQ (500) | ◯ | Δ |
| 12 | m-Phenylenediamine | PTZ | ◯ | X |
| 13 | " | PTZ (500) | ◯ | Δ |
| 14 | 2,4-Diaminotoluene | PTZ | ◯ | X |
| 15 | Not added | Not added | X | ◯ |

A: N,N'-Diphenyl-p-phenylenediamine
B: N,N'-Ditolyl-p-phenylenediamine
C: N,N'-Di-β-naphthyl-p-phenylenediamine
D: N-Phenyl-N'-isopropyl-p-phenylenediamine
E: N-Phenyl-N'-(1,3-dimethylbutyl)-p-phenylenediamine
F: N-(p-Methoxyphenyl)-p-phenylenediamine
G: p-Phenylenediamine
MEQ: Hydroquinone monomethyl ether
PTZ: Phenothiazine

EXAMPLE 12

Crude methacrylic acid obtained in the same manner as in Example 3 was continuously distilled at a reduced pressure of 50 mmHg and a reflux ratio of 0.5 in a 20-stage Oldershaw column, thereby separating methacrylic acid from high boiling components. The methacrylic acid contained 50 ppm of maleic acid, 30 ppm of furfural, 50 ppm of benzaldehyde, and 100 ppm of hydroquinone monomethyl ether as a polymerization inhibitor. Portions of the methacrylic acid were each added with fivefold moles of one of m-aminophenol, m-phenylenediamine and 2,4-diaminotoluene as additive compounds in combination with 300 ppm of one of N,N'-diphenyl-p-phenylenediamine, N-phenyl-N'-isopropyl-p-phenylenediamine and N-phenyl-N'-(1,3-dimethylbutyl)-p-phenylenediamine. Each of the resultant mixtures was continuously distilled in the above-described 20-stage Oldershaw column similarly. In all the 9 combinations of the additive compounds and polymerization inhibitors, there was no precipitation of polymerized substance so that continuous distillation was feasible for 10 hours or longer. The −log T of each methacrylic acid fraction thus obtained was 0.05 or smaller. In contrast, precipitation of polymerized matter started immediately after the initiation of distillation when hydroquinone monomethyl ether or phenothiazine was used in a proportion of 300 ppm.

We claim:

1. In a process for the purification of methacrylic acid by distilling crude methacrylic acid obtained by the vapor-phase catalytic oxidation of isobutylene, t-butanol, methacrolein or isobutylaldehyde with specific amines to obtained purified methacrylic acid, the improvement comprising:
    initially distilling said crude methacrylic acid in a distillation column and withdrawing a fraction from an intermediate stage of an enriching section of the distillation column;
    contacting said distilled crude methacrylic acid with at least one amine compound selected from the group consisting of m-aminophenol, m-phenylenediamine, 2,4-diaminotoluene and 2,4- diaminodiphenylamine in the presence of at least one p-phenylenediamine of formula (I):

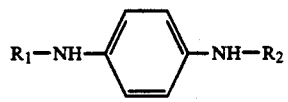

wherein $R_1$ is hydrogen, $C_3$-$C_6$-alkyl, phenyl, p-tolyl, p-methoxyphenyl or β-naphthyl and $R_2$ is hydrogen, phenyl, p-tolyl or β-naphthyl in a molar amount ranging from 3-10 times based on the carboxylic acid groups derived from unsaturated dibasic acids and aldehyde groups at a temperature ranging from 50°-100° C.; and distilling said crude methacrylic acid contacted with said at least one amine to prepare purified methacrylic acid.

2. The process as claimed in claim 1, wherein the intermediate stage of the enriching section of the distillation column is located between a top of the distillation column and a feeding port of the distillation column at a height ¼-¾ the way down from the top of the distillation column toward the feeding port of the distillation column.

3. The process as claimed in claim 1, wherein the latter distillation is carried out in the presence of at least one p-phenylenediamine represented by the following general formula (I):

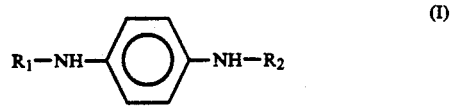

wherein $R_1$ means a hydrogen atom or a $C_3$-$C_6$-alkyl, phenyl, p-tolyl, p-methoxyphenyl or β-naphthyl group and $R_2$ denotes a hydrogen atom or a phenyl, p-tolyl or β-naphthyl group.

4. The process as claimed in claim 3, wherein said at least one p-phenylenediamine is present in a total amount of 0.005-1.0 wt. % based on the fraction.

* * * * *